United States Patent [19]

Woolson

[11] Patent Number: 4,841,975

[45] Date of Patent: Jun. 27, 1989

[54] PREOPERATIVE PLANNING OF BONE CUTS AND JOINT REPLACEMENT USING RADIANT ENERGY SCAN IMAGING

[75] Inventor: Steven T. Woolson, Los Altos, Calif.

[73] Assignee: Cemax, Inc., Santa Clara, Calif.

[21] Appl. No.: 38,515

[22] Filed: Apr. 15, 1987

[51] Int. Cl.$^4$ .............................................. A61B 6/00
[52] U.S. Cl. ................................... 128/653; 378/205; 128/303 B
[58] Field of Search ............ 378/205; 128/630, 303 B, 128/653, 659

[56] References Cited

U.S. PATENT DOCUMENTS

| 3,941,127 | 3/1976 | Froning | 128/303 B |
| 4,058,114 | 11/1977 | Soldner | 128/303 B |
| 4,360,028 | 7/1982 | Barbier et al. | 128/659 |
| 4,436,684 | 3/1984 | White | 264/138 |
| 4,440,168 | 4/1984 | Warren | 128/303 B |
| 4,583,538 | 4/1986 | Onik | 128/303 B |

OTHER PUBLICATIONS

Rutkow et al., "Orthopaedic Operations in The United States", *The Journal of Bone and Joint Surgery,* vol. 68-A, #5, 6/86, pp. 716–719.

Insall et al., "The Total Condylar Knee Prosthesis in Gonarthrosis", *The Journal of Bone and Joint Surgery,* vol. 64-A, #5, 6/83, pp. 619–628.

Lotke et al., "Influence of Positioning of Prosthesis in Total Knee Replacement", *The Journal of Bone and Joint Surgery,* vol. 59-A, #1, 1/77, pp. 77–79.

Johnson et al., "The Distribution of Load Across the Knee, A Comparison of Static and Dynamic Measurements", *The Journal of Bone and Joint Surgery,* vol. 62-B, #3, 8/80, pp. 346–349.

Corcoran, "Medical Electronics", *IEEE Spectrum,* 1/87, pp. 66–68.

McDonnell Douglas advertisement, "Breadthrough: Computer Graphics that Create Model Patients for Surgeons", *Businessweek,* 6/18/84.

"Machine-Made Body Joints", Science Digest, 6/83.

Love, "Better Bones", Forbes, 11/21/83, pp. 314, 316.

"Hospital for Special Surgery Computer Designs Customized Joint Replacements", Orthopedics Today, vol. 2, No. 12, 12/83, pp. 3 & 16.

*Primary Examiner*—Ruth S. Smith
*Attorney, Agent, or Firm*—Cushman, Darby & Cushman

[57] ABSTRACT

A method is disclosed for the preoperative planning of a total knee replacement. Guide tools having guide members which are adjustable for placement on selected positions of the femur and tibia are used for locating the position of desired bone cuts defined by a cutting guide surface existing on the guide member. Selected regions of the femur and tibia are scanned by computed tomographic techniques to provide images of these regions. The respective centers of the femur head, distal femur, proximal tibia and distal tibia, or ankle joint are determined. The center points are then used to define a mechanical axis relative to which selected cuts are to be made corresponding to selected prostheses to be implanted. The CT scan representations are used to measure the desired location of the guide member cutting surface and the respective locations of guide members adjacent selected bone positions. These guide members are adjusted relative to the cutting surface prior to surgery. This provides for precise placement of the guide tools during surgery and the making of accurate and precise bone cuts conforming to the selected prostheses.

18 Claims, 4 Drawing Sheets

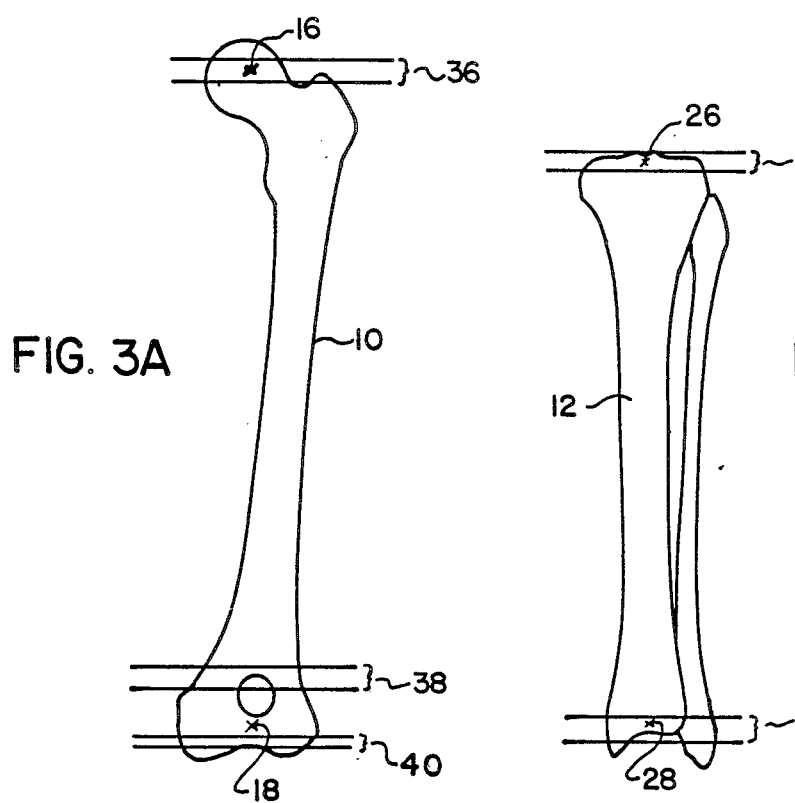
FIG. 3A
FIG. 3B
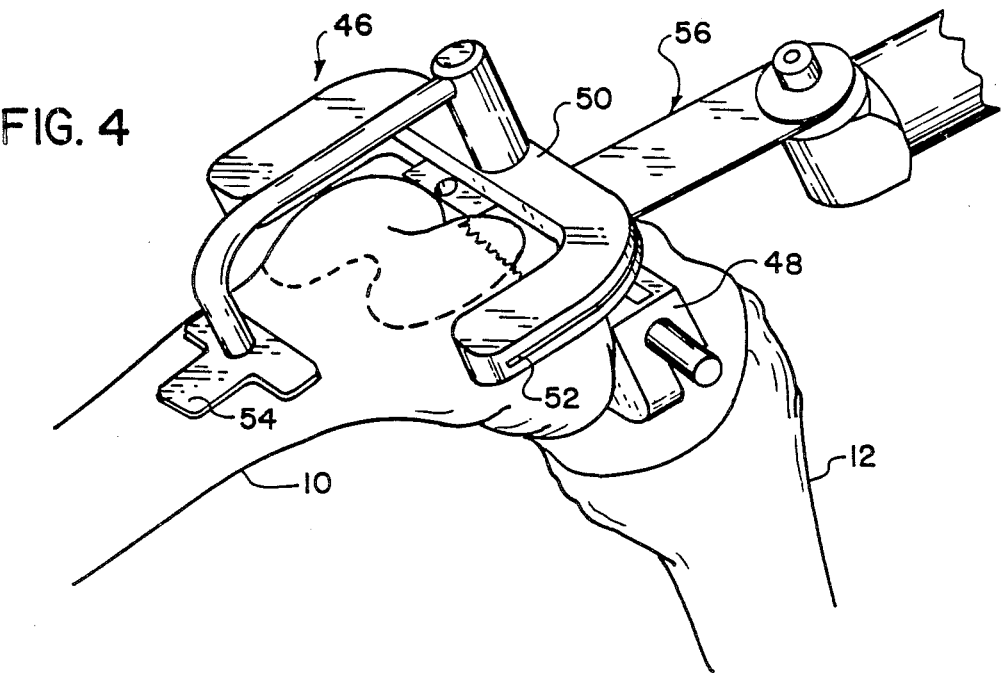
FIG. 4

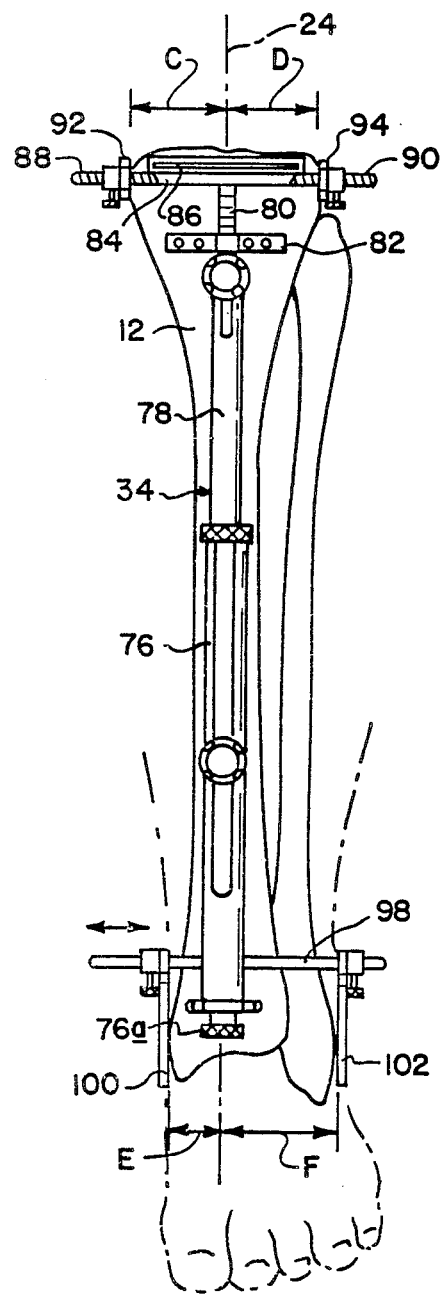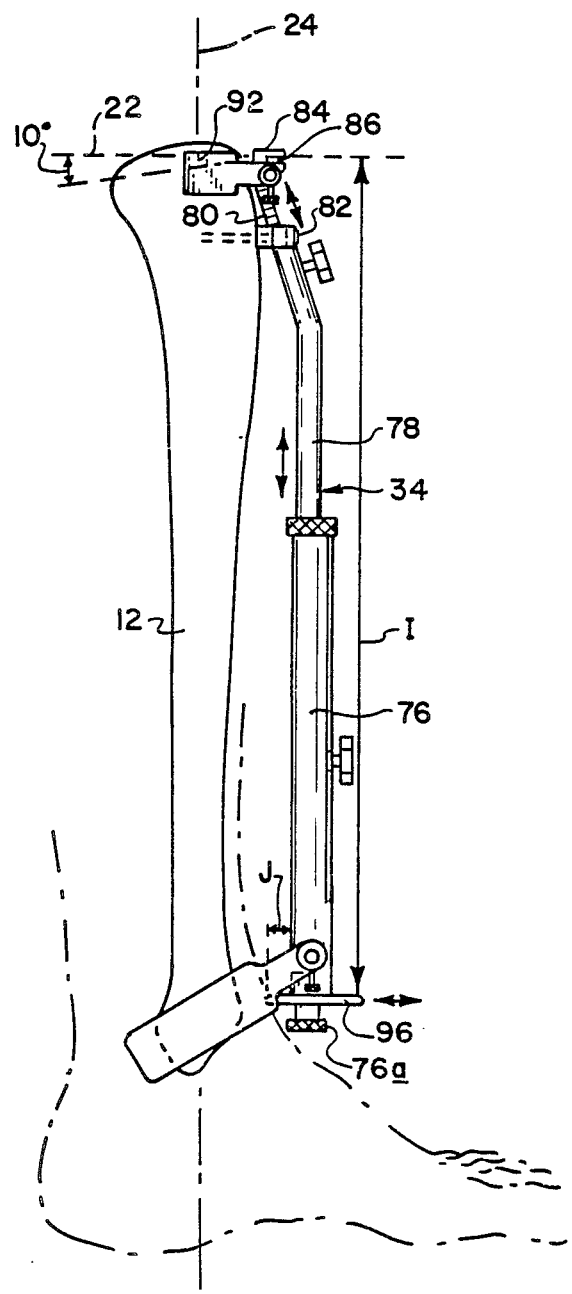
FIG. 8A
FIG. 8B

PREOPERATIVE PLANNING OF BONE CUTS AND JOINT REPLACEMENT USING RADIANT ENERGY SCAN IMAGING

BACKGROUND AND SUMMARY OF THE INVENTION

This invention relates to a method for preoperative planning of surgery. More particularly, it pertains to a method of preoperative planning of a bone cut and joint replacement using radiant energy scan imaging to determine the position of a bone-cut-defining guide relative to the bone to be cut.

The preferred method of the present invention is for the replacement of a total knee. This includes the removal of bone sections from the distal femur and proximal tibia for replacement by a knee joint prosthesis associated with each of these bones.

Total knee replacement is a common orthopaedic surgical procedure currently performed over 150,000 times each year in the U.S. The clinical results of many operations are excellent with complete relief of pain, improvement in function, restoration of motion, and correction of deformity in over 90% of the cases. However, there are a number of cases in which failures occur following the knee replacement. One of the most important causes for failure of the procedure is from prosthesis component loosening because of unbalanced loading of the tibial component caused by improper knee joint alignment. Because of this fact, all total knee implantation systems attempt to align the reconstructed knee joint in the mechanical axis in both the coronal and the sagittal planes. If achieved, this results in the placement of the total knee prostheses in a common mechanical axis which correspondingly is highly likely to produce a successful long-term result.

Reproducing the mechanical axis at surgery is presently done by one of two different techniques, which use either the external bone landmarks at the hip and ankle joints or the medullary canal of the femur or a combination of these two systems for alignment. Knee systems which use the center of the femoral head as a landmark for orienting the femoral component require an operative radiograph of the hip joint to position an external marker for alignment of the femoral cutting guide. Intramedullary knee systems require a preoperative radiograph of the femur in order to determine the angle between the anatomical and the mechanical axes of the femur for proper orientation of the femoral cutting guide. These intramedullary systems require the surgeon to estimate the placement of a drill hole into the distal femur at a central location in the bone for introduction of a small diameter rod into the medullary canal to produce the correct component alignment. The proximal tibia is cut perpendicular to the mechanical axis of the tibia by adjusting the tibial cutting guide in relation to the knee and ankle joints. Both of these techniques necessitate intraoperative visual estimation of the location of the midpoints of the distal femur, the proximal tibia and the ankle joint by the surgeon. The alignment of the components in the sagittal plane is also done by visual means or the "eyeball" method.

In summary, with the present total knee instrument systems, correct knee alignment involves the following:
1. preoperative determination of the angle between the anatomical and mechanical axes of the femur from the radiographs, and appropriate placement of the medullary rod entrance hole in the femur for the intramedullary system of femoral component alignment;
2. localization of the center of the femoral head by external markers after operative radiographs are taken, and correct estimation of the center of the distal femur for the external alignment system of femoral alignment;
3. visual estimation of the centers of the proximal tibia and of the ankle joint in both the coronal and sagittal planes for correct tibial component alignment.

These alignment techniques may produce error from the fact that the surgeon must estimate the correct position of all bone landmarks and from inaccuracies in the preoperative radiographs of the knee joint. Flexion contractures of the knee will cause significant errors in the tibiofemoral angle (the angle between the femoral anatomical and mechanical axes). Medullary systems require accurate placement of the entrance hole for the alignment rods since the rod does not tightly fit into the medullary canal and may be angled into it if the drill hole is placed too far medially or laterally. A considerable amount of the operative time in total knee replacement surgery is expended in positioning and attaching the alignment instruments and in double-checking their placement, which is essential since any system may fail and have to be overruled by the experienced eye of the surgeon.

The present invention overcomes the inherent inaccurateness of the presently used systems by combining several steps. Selected regions of the body adjacent a bone to be resectioned are scanned with radiant energy to obtain representations of the regions for defining the structure of the specific bone and adjacent body regions. From the representations, desired positions of a cutting guide relative to the bone are determined. Thus, by having these specific features of bone structure identified and used for determining specific placement of the cutting guide, accurate and precise placement during the surgical procedure is provided.

Control of the guide surface of a cutting guide which defines the contour of a desired bone cut is assured where the cutting guide includes one or more gauge members positionable adjacent a selected position on the bone and adjustable relative to the guide surface for positioning the guide relative to the bone. These specific settings of the gauge members relative to the guide surface are determined from the representations of the selected body regions adjacent and including the bone having a section to be replaced. In the preferred method of the present invention, a joint is replaced and the replacing prostheses are aligned relative to axes associated with each joint-forming bone so that the resulting prostheses will have a specific alignment relative to those axes. By determining the position of the gauge member relative to the axis, the position of the cutting guide surface is established prior to the surgical procedure, with corresponding precise placement of the guide during the procedure.

It should be noted that CT scan information has been used in the past relative to prostheses. For example, in an article in Volume 97 (June 1979) of *Fortschritte der Medizin* on page 781–784 entitled "Ein neues Verfahren zur Herstellung Alloplastischer Spezilimplantate fur den Becken-Teilersatz", a method of preparing alloplastic implants is described in which a three-dimensional model of a patient's pelvis is constructed by assembling styrofoam sheets made from computer tomography films. U.S. Pat. No. 4,436,684 assigned to the same assignee as this application, describes using information obtained from CT scans to drive a sculpting tool to make a corporeal model.

As will be more apparent hereinafter, with the present invention a surgeon's need to do preoperative planning from plain radiographs is eliminated. Because there is no need to determine the placement or adjustment of cutting guides at the time of surgery, fewer instruments are necessary and the surgical procedure is simplified and shortened. Accurate sizing of the prosthesis components is possible by measurement of the axial CT scan slices at the level of component placement for each bone. The vast majority of all important intraoperative decisions are decided preoperatively by this intensive and precise planning method. The surgeon has to make fewer critical judgment calls during surgery and is able to eliminate the constant visual monitoring of the alignment instrument. Elimination of these steps markedly reduces the operative time of the procedure.

BRIEF DESCRIPTION OF THE DRAWINGS

Referring now to the accompanying four sheets of drawings:

FIGS. 3A, 3B are silhouette views of a femur and a tibia, respectively, identifying bone regions scanned for obtaining representations of the bones;

FIG. 4 is a perspective view of an anterior femoral cutting guide in place on a distal femur;

FIGS. 8A, 8B show anterior and lateral views, respectively, of a proximal tibial cutting guide in position adjacent a tibia showing adjustments and placement of the cutting guide for use during a knee replacement operation performed according to the present invention.

DETAILED DESCRIPTION OF THE PREFERRED METHOD

The preferred method of practicing the present invention is based on exact three-dimensional (3D) data of the bone anatomy obtained from computed tomography (CT) scans of the knee, hip and ankle joints for a total knee replacement. Any point on a CT scan slice can be located on the x or horizontal axis (coronal plane) and on the y or vertical axis (sagittal plane) as seen on a two-dimensional (2D) CT image. Specific points may be located by scaling or measuring relative to a reference point on the 2D image. Alternatively, such points may be simply identified on a CT scan imaging system, such as a CEMAX-1000 or CEMAX-1500 system available from CEMAX, Inc. of Santa Clara, Calif. In such system, the image generated from CT scan information is identified by movement of a cursor to the specific point of interest. The system then determines the spatial or 3D coordinates associated with that point which then may be related to any other point selected which resulted from the same scan procedure, so long as the patient has not been moved. Thus, it will be appreciated that the points, lines and dimensions discussed herein may be obtained either in a manual process using reproduced selected 2D images, or by identifying those points on an appropriate computer system which then can relate the specific points selected.

Figure 1:
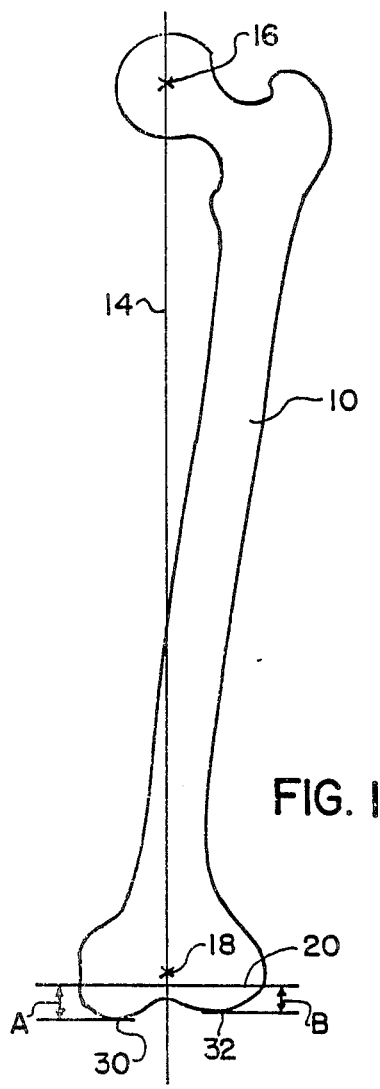
FIG. 1 is a silhouette view of a femur as viewed in the coronal plane.
Figure 2A:
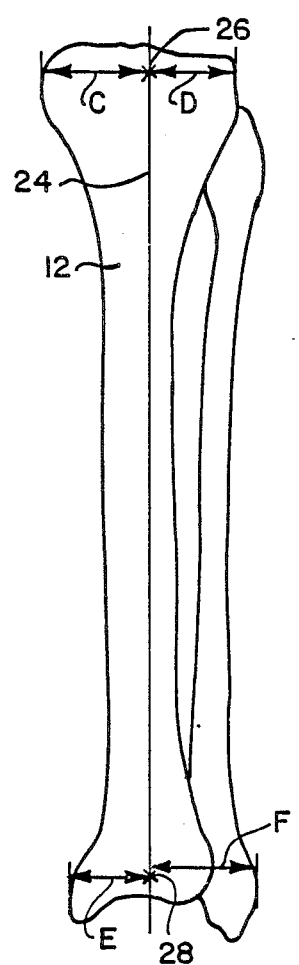
FIGS. 2A, 2B are silhouette views of a tibia in coronal and sagittal planes, respectively.
Figure 2B:
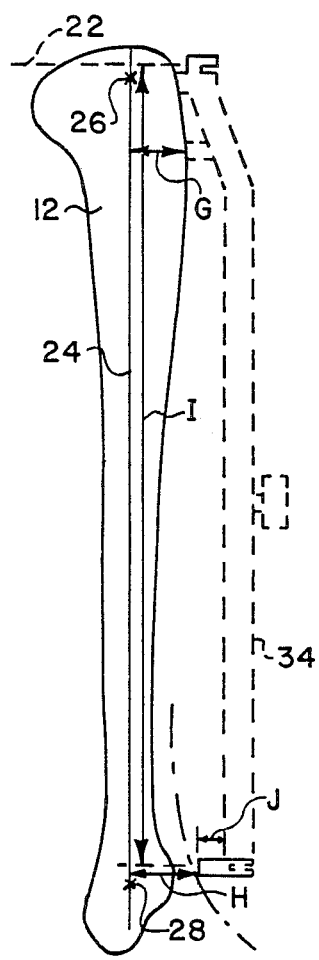

Referring initially to FIGS. 1, 2A and 2B, selected positions on the bones of interest, in this case the femur and tibia, are identified. In this instance it is important that the knee prostheses be positioned on, and for relative rotation about, an axis perpendicular to the mechanical axis of a femur 10 and a corresponding tibia 12. A mechanical axis 14 extends through the midpoint 16 of the femur head. Axis 14 also extends through midpoint 18 of the distal femur. During the knee replacement surgical procedure, it will be necessary to resection the medial and lateral condyles of the distal femur by cutting along a line 20 which is perpendicular to axis 14.

The proximal end of tibia 12 will be resectioned along a cut plane identified by the dashed line 22 in FIG. 2B. The line of this cut must be perpendicular, or slightly angled as will be discussed subsequently, relative to a mechanical axis 24 of the tibia. Axis 24 is defined by the midpoint 26 of the proximal tibia and the midpoint 28 of the ankle joint.

The mechanical axes of the femur and tibia in two planes can be graphically determined by identification of the 3D coordinates derived from the CT image data by identification of the positions of the midpoints of the femoral head, the distal femur, the proximal tibia and the ankle joint in the coronal and sagittal planes. Further, the 3D spatial location of the most distal projections of the medial and lateral femoral condyles 30, 32, respectively, are found in the coronal plane image, as shown in FIG. 1. The distance from each of these points to distal femoral cut line 20 is also determined. These are represented, respectively, by distances A and B. This gives the proportions of bone from the medial and lateral condyles which are to be resected to produce a distal femoral cut along line 20. As will be seen, the plane represented by line 20 in FIG. 1 is also perpendicular to the anterior femoral cortex which, in the sagittal plane, is parallel with mechanical axis 14. The remainder of the femoral bone cuts, as will be described, are customized to the specific prosthesis, and ligamentous balancing of the new knee joint is done in a routine manner.

As will be seen, the tibial cutting guide includes gauge members positioned to contact opposite sides of the proximal tibia and, with an allowance for skin depth, the lateral and medial ankle protusions. More specifically, tibial mechanical axis 24 in the coronal and sagittal planes, as seen in FIGS. 2A, 2B, is graphically depicted and the distances from this line are found to the medial cortex (distance C) and to the lateral cortex (distance D) of the proximal tibia. Also the distance from mechanical axis 24 to the skin surface over the medial malleolus (distance E) and to the skin surface over the lateral malleoulus (distance F) are determined for alignment in the coronal plane. Further, from a representation of the tibia in the sagittal plane, the distance from the axis to the anterior cortex of the proximal tibia where the tibial cutting guide 34 contacts it (distance G) and the distance from the axis to the skin surface over the anterior aspect of the distal tibia (distance H) is determined. Further, the distance along axis 24 from cut line 22 to the position where distance H is measured, is also determined. This distance is shown as distance I.

Finally, as will be further described subsequently, the position of the base of tibial cutting guide 34 from the skin surface over the anterior aspect of the distal tibia can be varied to control the angle of cut line 22 with respect to axis 24. Thus, a distance J must be determined for producing the corresponding selected angle.

In order to obtain the necessary representations or images of the regions of the femur and tibia, and associated body portions, such as the skin around the ankle, suitable CT scans are made. Further, since only selected regions need be measured, only those regions need to be scanned. The CT scan protocol involves independent scans of the femur and of the tibia with the patient supine and with the knee joint in extension. The femoral scan includes a single centimeter-thick scan through the center of the femoral head as identified by region 36 of FIG. 3A. With the femur held in position, a single 1-centimeter-thick scan is made through the distal femur, in region 38, through the femoral condyles at the midpoint of the patella. Then 1.5- or 2-millimeter-thick scans are performed through the distal projections of both femoral condyles, shown as region 40, so that the most detailed information is of the articular surface of the femur.

The patient is repositioned for the scans of the tibia. A single centimeter thick scan through the ankle joint (region 42) is made and again, without any patient motion, the proximal articular surface of the tibia is similarly scanned (region 44).

When an enhanced computerized imaging system is used, a magnetic tape copy of the CT image data is made for transfer of the data to the imaging system for producing the representations of the selected bones.

From the spatial coordinates in the coronal plane derived from the scans of the femoral head and the distal femur, a femoral coronal mechanical axis line 14 is mapped out on graph paper as illustrated in FIG. 1. Distal femoral cut line 20 is drawn perpendicular to mechanical axis line 14. Measurements of the distances from line 20 to the most distal points 30, 32 on the medial and lateral femoral condyles, respectively, are taken from the graph. The relative distances for medial and lateral condylar bone resection to create a distal femoral cut along line 20 are thus known. This bone cut is also made perpendicular to the anterior femoral cortex, and therefore, the distal femoral cut need only be planned in the coronal plane.

Planning of the proximal tibial cut is more complex, since the reference points for it must be determined in two planes preoperatively. The tibial mechanical axis 24 in the coronal and sagittal planes is determined from the coordinates of the centers of the ankle joint (point 28) and of the proximal tibia (point 26). The distances from this axis to the medial (distance C) and lateral (distance D) cortexes of the proximal tibia and to the skin over the medial (distance E) and lateral (distance F) malleolus are used for appropriate positioning of the tibial jig or cutting guide 34 in the coronal plane. It will be appreciated that any two of these distances are sufficient to align the tibial jig relative to the axis.

The direction of the proximal tibial cut in the sagittal plane will be dependent upon the particular total knee prostheses chosen. This cut may be made perpendicular to the sagittal mechanical axis, as is shown in FIG. 2B, or inclined posteriorly up to 5 or 10 degrees. The distance from the skin surface over the distal tibial plafond to the distal portion of the tibial cutting guide (distance J) determines the amount of posterior inclination of the tibial cut.

Using this preoperative planning method, the surgeon is able to determine mechanical axes 14, 24 and distances A–J. These specific bone landmarks and distances correspond for presetting the cutting guides illustrated in FIGS. 4–8, which now will be discussed. It will be appreciated that the various cutting guide adjustments which need to be made are precisely determined. The gauge members of the guides are adjusted corresponding to the determined distances. Thus, when these cutting guides are placed in position adjacent the bone to be resectioned, precise positioning and alignment are achieved.

Figure 5:
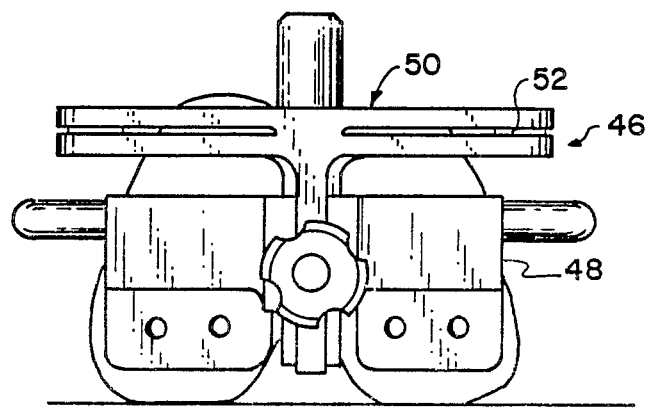
FIG. 5 is a distal end view of the cutting guide of FIG. 4.

In particular, during a surgical procedure, the first femoral bone cut is flush with and parallel to the anterior cortex of the femur as illustrated in FIGS. 4 and 5. In these figures, the position of an anterior cortex cutting guide 46 is shown positioned on the distal end of a femur 10. Guide 46 includes a block member 48 which is tacked into position against the distal condyles as shown in the figures. A cutting-surface-defining member 50 has a slit 52 which is planar and aligned with the underside of a foot 54 positionable on the anterior tibial cortex. Thus, a saw 56 cutting through slit 52 makes an initial anterior femoral cut flush with the anterior femoral cortex, as shown by the dashed lines in FIG. 4. This results in a bone surface which is parallel with the anterior femoral cortex which, as discussed previously, is parallel with the mechanical axis of the femur.

Figure 6A:
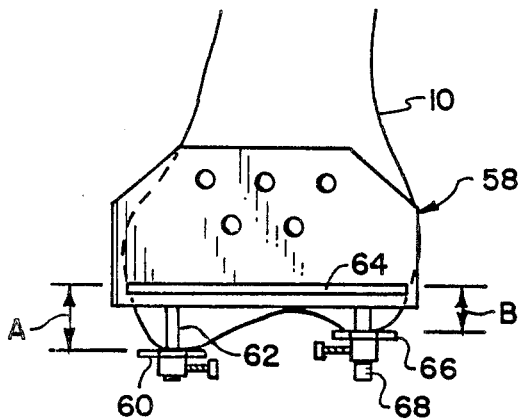
FIGS. 6A, 6B are anterior and lateral views, respectively, of a femur with a distal femoral cutting guide in place.
Figure 6B:
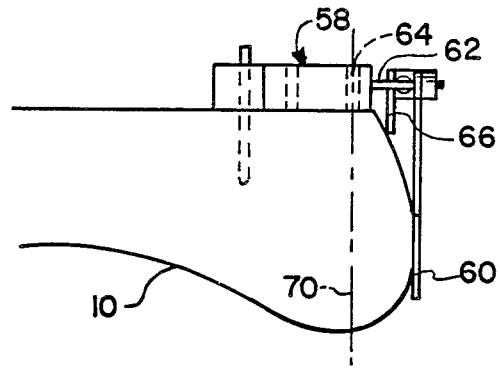

As illustrated in FIGS. 6A and 6B, the distal femur condylar cuts are then made using a distal femoral cutting guide 58 placed flat on the anterior femur surface just cut and pinned into place. The proportion of the medial and lateral femoral condylar bone to be resected which was determined by the preoperative planning system is used to set this instrument. If, for example, this proportion is 2:1, or removal of twice the amount of medial femoral condylar bone as lateral femoral condylar bone, and the distal thickness of the femoral prosthesis is 8 mm, then the distal femoral cutting guide gauge member 60 is correspondingly adjustably positioned on an adjustment post 62 relative to a slit 64 defining a cut surface contour (corresponding to cut line 20). Correspondingly, the lateral femoral condyle cut is determined by positioning a gauge member 66, which extends down across the face of the condyle, a distance B from slit 64, by adjustment along an adjustment post 68. With the bottom surface of cutting guide 58 being planar and perpendicular to slit 64, a cut, identified by line 70 in FIG. 6B, results which is perpendicular to mechanical axis 14.

Figure 7A:
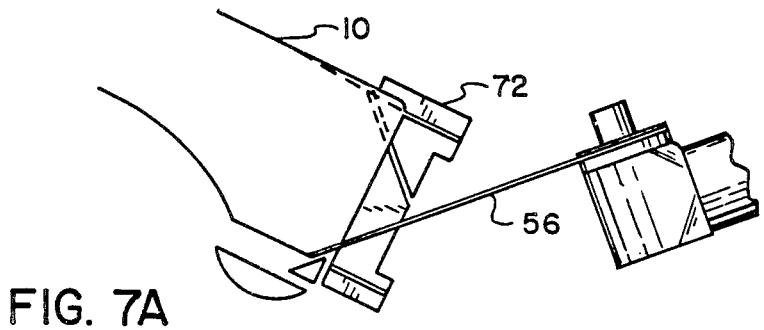
FIGS. 7A, 7B are a lateral view and a perspective of another cutting guide for making final femoral cuts.
Figure 7B:
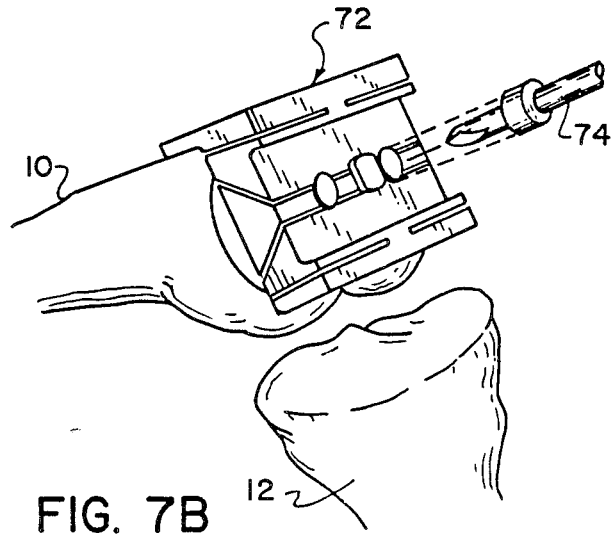

The final anterior, posterior and chamfer cuts on the femur are made after the proximal tibial cut has been made and a trial test of adequate bone resection has been made with the knee in extension using trial spacers, as is conventionally done. The final distal femoral cuts are made with a single conventional cutting guide 72 which is fixed in position on femur 10 by pins which are placed in holes drilled in the end of the femur which correspond to the pegs in the actual femoral prosthesis, as represented by the use of a drill 74. The resulting cuts by saw 56 are illustrated in FIG. 7A.

FIGS. 8A, 8B illustrate the positioning of tibial cutting guide 34 relative to tibia 12. Cutting guide 34 includes a telescoping shaft, parallel with axis 24 as viewed in FIG. 8A, consisting of a base member 76, an intermediate shaft member 78, and a cut-positioning member 80. Each of these three members are adjustable relative to the other, as shown. Intermediate member 78 includes a brace 82 which contacts the anterior cortex of the proximal tibia. This position corresponds with the location for measuring distance G described with reference to FIG. 2B. Further, cut-positioning member 80 has a cross-arm 84 with a slit 86 defining the proximal tibial cut. Cross-arm 84 includes laterally extending adjustment bars 88, 90 to which are adjustably attached corresponding gauge members 92 and 94, respectively. These gauge members are positioned relative to shaft member 80 in accordance with dimensions C and D, as described previously. At the end of base shaft member 76 opposite from intermediate shaft member 78 is a plate 96 which is adjustable relative to shaft member 76 for varying the distance of the associated end 76a of the base shaft member from the skin surface over the anterior aspect of the distal tibia, as discussed previously. End 76a is also referred to herein as a gauge member. Thus, plate 96 is adjustable for positioning the end 76a a distance J from the skin surface.

Mounted on base shaft member 76 adjacent end 76a is a lateral adjustment bar 98 which extends to each side of shaft member 76, as shown in FIG. 8A. Each end of bar 98 has an ankle joint gauge member. A gauge member 100 is positioned a distance E for placement on the skin over the medial malleolus. The other gauge member 102 is positioned a distance F from the longitudinal axis of shaft member 76 for placement on the skin over the lateral malleolus. Thus, the adjustments of the various gauge members as well as the length of the shaft members result in cutting slit 86 being aligned perpendicular to mechanical axis 24. Thus, cutting guide 34 is aligned precisely relative to the tibia.

The posterior inclination of the tibial bone cut is determined by the design requirements of the particular prosthesis. Adjustable plate 96 on shaft end 76a, as has been discussed, is set at a distance which will result in the desired posterior inclination of the angle of proximal tibial bone cut defined by slit 86. It is sufficient, to align tibial cut line 22 below the most deficient tibial plateau as determined by the CT scan representations. Cutting guide 34 is then stabilized in the proximal tibia by pins shown in dashed lines in brace 82. The bone cut is made along cut line 22 by passing a saw 56 through slit 86. The posterior cruciate ligament may be removed or spared according to the surgeon's preference. After making the tibial and the distal femoral bone cuts, a trial tibial component and trial femoral spacer is inserted into the joint space to test the adequacy of bone resection with the knee in extension, as is conventionally done. If this space is inadequate, further resection of the distal femur is possible before the remaining femoral bone cuts are made.

The remainder of the surgical procedure is carried out as usual. The patella is prepared, trial components are inserted, and soft-tissue balancing is done by varying the thickness of the tibial component or by ligamentous release procedures. The actual prostheses are selected and implanted.

It is seen that this preoperative CT planning method produces distal femoral and proximal tibial bone cuts which are perpendicular to the coronal mechanical axis without intraoperative localization of the femoral head or other external bone landmarks. Positioning of alignment instruments in relation to the hip joint or femoral medullary canal at surgery is not needed, since all landmarks for these bone cuts are at the knee and ankle joint.

The above discussion is directed specifically to a preferred method of practicing the invention. However, it will be appreciated that the method has general applicability to any bone resectioning in which the bone cuts are defined by a cutting guide surface of a guide member placeable adjacent the bone for guiding the resectioning. Thus, while a preferred method of practicing the invention has been described, it will be understood by those skilled in the art that various changes may be made without departing from the spirit and scope of the invention as defined by the claims and their equivalents.

What is claimed is:

1. A method of preoperative planning of surgical cuts of a selected bone in a body using a cutting guide having a guide surface defining the contour of a desired bone cut and a gauge member having a predetermined position relative to the guide surface and positionable adjacent a selected postion on the bone, comprising:

selecting regions of the body in which the selected bone is located to be used in determining a desired positioning of the cutting guide relative to the bone during cutting;

subjecting the selected body regions to radiant energy to produce radiant energy responses that are characteristic of the body and the selected bone and are detectable externally of the body;

detecting produced radiant energy responses to obtain representations of the selected body regions, including representations of the corresponding regions of the individual bone; and determining from the representations a selected position of the gauge member relative to the bone so that when the gauge member is placed adjacent the selected position on the bone, the guide surface is in the selected position relative to the bone.

2. A method according to claim 1 wherein the gauge member is adjustable relative to the guide surface for positioning the guide surface relative to the bone, said determining from the representations further including adjusting the gauge member relative to the bone so that when the gauge member is placed adjacent the selected position on the bone, the guide surface is in the selected position relative to the bone;

said method further including adjusting the position of the gauge member relative to the guide surface corresponding to the determined position so that the guide surface is in the selected position when the cutting guide is placed adjacent the bone.

3. A method according to claim 2 usable when a surgical cut is desired having a selected orientation relative to a definable axis associated with the bone and the cutting guide has a plurality of gauge members;

said selecting including selecting regions of the bone relative to which the position of the axis can be determined;

said determining further including determining the desired positions of the gauge members relative to the bone appropriate for positioning the guide surface in the desired position relative to the axis; and said adjusting including adjusting the position of the gauge members relative to the guide surfaces corresponding to the determined positions so that the guide surfaces are positioned relative to the axis when positioned with the gauge members adjacent the bone.

4. A method according to claim 3 which further includes producing three-dimensional coordinates corresponding to portions of the axis relative to a plurality of the regions subjected to radiant energy.

5. A method according to claim 2 wherein the cutting guide has a plurality of such adjustable gauge members;
said determining further including determining the positions of placement of the gauge members adjacent the bone appropriate for positioning the guide surface in the selected position relative to the bone; and
said adjusting further including adjusting the positions of the gauge members relative to the guide surface according to the determined positions.

6. A method according to claim 1 usable for planning replacement of a section of bone with a prosthesis having a selected bone interfacing surface, and wherein the cutting guide has a surface defining the contour of said bone interfacing surface;
said selecting including selecting the regions of the bone to be cut to mate with the selected bone interfacing surface; and
said determining further including determining the position of the cutting relative to the bone so that the guide surface is aligned with the bone for cutting to produce a bone surface to mate with said selected bone interfacing surface of the prosthesis.

7. A method of preoperative planning of surgical joint replacement using bone-cutting guides, which joint has adjacent bone ends and each guide has a guide surface defining the contour of a desired bone cut and a gauge member having a predetermined position relative to the guide surface and positionable adjacent a selected position on a bone, comprising:
choosing prostheses to be implanted on the adjacent bone ends for forming the replacement joint;
selecting regions of the body in which the bones forming the selected joint are located, which regions are to be used in determining the positions of the bone-cutting guides for cutting during surgery, bone cuts for forming bone surfaces conforming with corresponding surfaces of the prostheses;
subjecting the selected body regions to radiant energy to produce radiant energy responses that are characteristic of the body and the bones forming the joint and are detectable externally of the body;
detecting produced radiant energy responses to obtain representations of the selected body regions including representations of the corresponding regions of the individual bones; and
determining from the representations selected positions for the bone-cutting guides during cutting so that the protheses, when implanted on the resulting cut surfaces, form jointly the replacement joint.

8. A method according to claim 7 wherein it is desired to orient at least one of the prostheses relative to an axis associated with the bone to which the one prosthesis is to be attached;
said region selecting including selecting regions of the bone relative to which the position of the axis can be determined;
said determining including determining the position of the axis relative to the bone, determining the position of the proposed bone-cut relative to the axis, and determining the resulting position of the bone-cutting guide relative to the bone so that the cut to be guided by the bone-cutting guide has the desired orientation relative to the axis.

9. A method according to claim 8 wherein said determining positions from the representations includes determining at least two-dimensional coordinates defining the axis.

10. A method according to claim 7 wherein it is desired to align both bones along an intended common axis by corresponding placement of both prostheses relative to the respective bones;
said region selecting further including selecting regions of each bone relative to which the position of the axis relative to each bone can be determined;
said determining including determining the position of the intended common axis adjacent each bone, determining the positions of the respective bone cuts relative to the respective axis, and determining the resulting positions of the bone-cutting guides relative to the corresponding bones so that the corresponding cuts have the desired orientations relative to the resulting common axis.

11. A method according to claim 10 wherein the guides have guide surfaces defining the contour of desired bone cuts corresponding to the bone-interfacing surfaces of the prostheses and gauge members positionable adjacent selected positions on the respective bones and adjustable relative to the guide surfaces, for positioning the guide surfaces relative to the respective bones;
said position determining further including determining the positions of the gauge members relative to the guide surfaces so that when the gauge members are placed adjacent the selected positions on the bones, the guide surfaces are in the selected positions relative to the bones; and
adjusting the positions of the gauge members relative to the guide surfaces so that the guide surfaces are in the selected positions relative to the bones when the gauge members are placed adjacent the selected positions on the bones.

12. A method according to claim 11 wherein the joint to be replaced is a knee, the common axis is the mechanical axis and a femoral cutting guide is used having a planar guide surface and a pair of gauge members positionable respectively on the medial and lateral condyles;
said selecting further including selecting regions of the distal and proximal ends of the femur;
said determining positions from the representations including determining the positions of the midpoints of the femoral head and the distal femur in coronal and sagittal planes, these midpoints defining the mechanical axis of the femur, determining the most distal projection of each of the medial and lateral femoral condyles in a coronal plane, determining the distance from the most distal projection to each of the medial and lateral femoral condyles to a line perpendicular to the femoral mechanical axis in the coronal plane disposed proximally of the medial and lateral condyles, which line corresponds to a desired bone cut; and
adjusting the pair of femoral cutting guide gauge members according to the distances from the condyle projections to the line perpendicular to the mechanical axis so that the distance from the gauge members to the planar guide surface is equal to the respective determined distances from the condyle projections to the line perpendicular to the mechanical axis.

13. A method according to claim 12 which further includes a tibial cutting guide having a guide surface defining a bone cut contour and positionable adjacent the anterior cortex of the proximal tibia, and a pair of gauge members adjustable for positioning repectively adjacent a selected lateral cortex of the proximal tibia and to the skin surface over the medial malleolus and the lateral malleolus for aligning the guide surface in the coronal plane;

said selecting further including selecting regions of the distal and proximal ends of the tibia;

said determining positions from the representations including determining the positions of the midpoints of the proximal tibia and ankle joint in the coronal plane, these midpoints defining the mechanical axis in the coronal plane, determining the distance from the tibial mechanical axis to the elected lateral cortex of the proximal tibia, determining the distance from the tibial mechanical axis to the skin surface over the medial malleolus and the lateral malleolus and determining the desired position of the proposed bone cut defined by the guide surface relative to the tibial mechanical axis; and adjusting the pair of tibial cutting guide gauge members according to the respective determined distances for positioning the guide surface relative to the determined mechanical axis.

14. A method according to claim 11 wherein the joint to be replaced is a knee, the common axis is the mechanical axis, and a tibial cutting guide is used having a guide surface defining a bone cut contour and positionable adjacent the anterior cortex of the proximal tibia, and a pair of gauge members adjustable relative to the cutting guide surface for positioning respectively adjacent a selected one of the medial cortex and lateral cortex of the proximal tibia and to the skin surface over the medial malleolus and the lateral malleolus for aligning the guide surface in a coronal plane;

said selecting including selecting regions of the distal and proximal ends of the tibia;

said determining positions from the representations including determining the positions of the midpoints of the proximal tibia and ankle joint in a coronal plane, these midpoints defining the mechanical axis in the coronal plane, determining the distance from the tibial mechanical axis to the selected one of the medial cortex and lateral cortex of the proximal tibia, determining the distance from the tibial mechanical axis to the skin surface over the medial malleolus and lateral malleolus, and determining the desired position of the proposed bone cut defined by the guide surface relative to the tibial mechanical axis; and adjusting the pair of tibial cutting guide gauge members according to the respective determined distances for positioning the guide surface relative to the determined mechanical axis.

15. A method according to claim 11 wherein the joint to be replaced is a knee, the common axis is the mechanical axis, a tibial cutting guide has a cutting guide surface defining a bone-cut contour and positionable adjacent the anterior cortex of the proximal tibia, and a gauge member positionable adjacent the skin surface over the anterior aspect of the distal tibia and adjustable for varying the distance between the guide surface and gauge member for alignment along the mechanical axis;

said selecting including selecting regions of the distal and proximal ends of the tibia;

said determining positions from the representations including determining the distance between a selected position on the anterior cortex of the proximal tibia where the cutting guide surface is to be positioned and a selected position on the skin surface over the anterior aspect of the distal tibia adjacent to which the gauge member is to be positioned; and adjusting the distance between the cutting guide surface and the gauge member to correspond to the determined distance between the selected position on the anterior cortex of the proximal tibia and the selected position on the skin surface over the anterior aspect of the distal tibia.

16. A method according to claim 15 wherein the cutting guide is adjustable for varying the distance between the gauge member and the skin surface over the anterior aspect of the distal tibia for varying the angle of the cutting guide surface relative to the mechanical axis;

said determining positions from the representations including determining the distance between the gauge member and the position on the skin surface over the anterior aspect of the distal tibia for orienting the cutting guide surface relative to the mechanical axis at a selected angle.

17. A method according to claim 11 wherein said determining positions from the representations includes determining at least two-dimensional coordinates representing the selected positions adjacent the bones where the gauge members are to be positioned.

18. A method according to claim 7 wherein said subjecting and detecting are performed using computed tomographic techniques.

* * * * *